(12) United States Patent
Holdbrook

(10) Patent No.: US 8,688,415 B2
(45) Date of Patent: Apr. 1, 2014

(54) SYSTEMS AND METHODS FOR PERFORMING STRESS INTENSITY FACTOR CALCULATIONS USING NON-SINGULAR FINITE ELEMENTS

(75) Inventor: Stephen J. Holdbrook, Eastleigh (GB)

(73) Assignee: Kellogg Brown & Root LLC, Houston, TX (US)

( * ) Notice: Subject to any disclaimer, the term of this patent is extended or adjusted under 35 U.S.C. 154(b) by 243 days.

(21) Appl. No.: 13/019,457

(22) Filed: Feb. 2, 2011

(65) Prior Publication Data

US 2011/0191074 A1    Aug. 4, 2011

Related U.S. Application Data

(60) Provisional application No. 61/301,022, filed on Feb. 3, 2010.

(51) Int. Cl.
*G06F 7/60* (2006.01)
(52) U.S. Cl.
USPC .............................................. 703/2
(58) Field of Classification Search
USPC ................... 703/5–6, 10; 702/6–13; 73/152.01–152.62
See application file for complete search history.

(56) References Cited

U.S. PATENT DOCUMENTS

| | | | |
|---|---|---|---|
| 4,567,774 A | 2/1986 | Manahan et al. | |
| 6,460,012 B1 | 10/2002 | Welch et al. | |
| 6,704,693 B1 | 3/2004 | Fan et al. | |
| 6,813,949 B2 | 11/2004 | Masaniello et al. | |
| 7,016,825 B1 | 3/2006 | Tryon, III | |
| 7,328,625 B2 | 2/2008 | Sundermeyer et al. | |
| 7,480,601 B2 | 1/2009 | Tryon, III | |
| 8,204,727 B2 * | 6/2012 | Dean et al. | 703/10 |
| 2002/0013687 A1* | 1/2002 | Ortoleva | 703/10 |
| 2006/0089823 A1* | 4/2006 | Meyer et al. | 703/2 |
| 2011/0077918 A1* | 3/2011 | Mutlu et al. | 703/2 |

OTHER PUBLICATIONS

"Modeling cracks in arbitrarily shaped finite bodies by distribution of dislocation," Jian-Jun Han, Manicka Dhanasekar, Central Queensland University, Australia, Mar. 2003.*
"A Finite Element Method for Crack Growth Without Remeshing," Nicolas Moes, Hohn Dolbow, and Ted Belytschko, International Journal for Numerical Methods in Engineering, 1999.*
"Crack Modeling for Structural Health Monitoring," M. I. Friswell and J.E.T. Penny, University of Wales, School of Engineering and Applied Science, UK, 2002.*

(Continued)

*Primary Examiner* — Matt Kim
*Assistant Examiner* — Maryam Ipakchi
(74) *Attorney, Agent, or Firm* — Gary M. Machetta

(57) ABSTRACT

Systems and methods are disclosed for determining stress intensity factors. In one or more embodiments, the method can include the steps of defining a crack tip zone about one or more crack tips of one or more arbitrarily shaped cracks in an arbitrarily shaped solid. The one or more crack tip zones can be constrained within a finite element model representation mesh of the arbitrarily shaped solid to provide one or more constrained crack tip zones. The combination of the finite element model representation mesh and the one or more constrained crack tip zones can be processed to determine the stress intensity factor for each of the one or more arbitrarily shaped cracks.

17 Claims, 5 Drawing Sheets

(56) References Cited

OTHER PUBLICATIONS

"On the Modified Westergaard Equations for Certain Plane Crack Problems," J. Eftis and H. Liebowitz, School of Engineering and Applied Science, The George Washington University, Washington DC (Mar. 31, 1972), Int. Journal of Fracture Mech. (1972), pp. 383-392.*

J. Eftis and H. Liebowitz, On the Modified Westergaard Equations for Certain Plane Crack Problems, in International Journal of Fracture Mechanics, Dec. 1972, pp. 383, 387 and 388, vol. 8, No. 4, The Netherlands.

Guide to Methods for Assessing the Acceptability of Flaws in Metallic Structures in British Standard, BS 7910:2005, pp. 184-193.

* cited by examiner

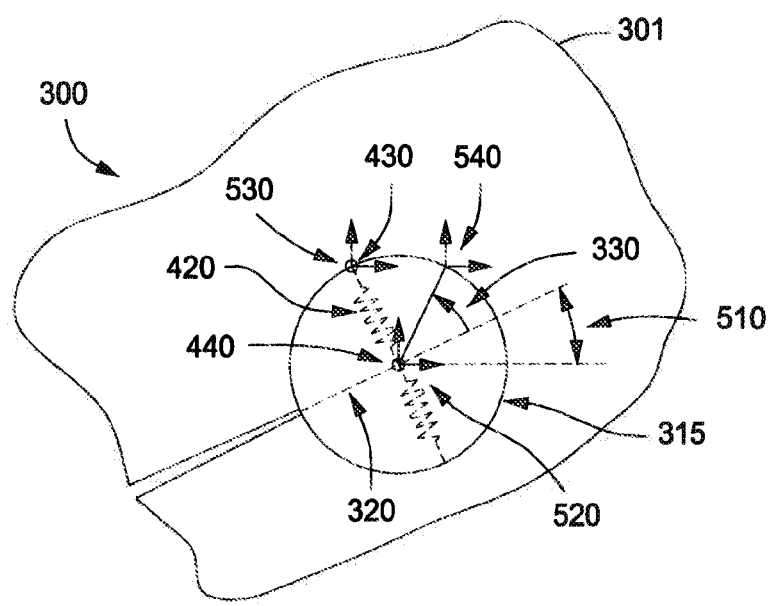
FIG. 5
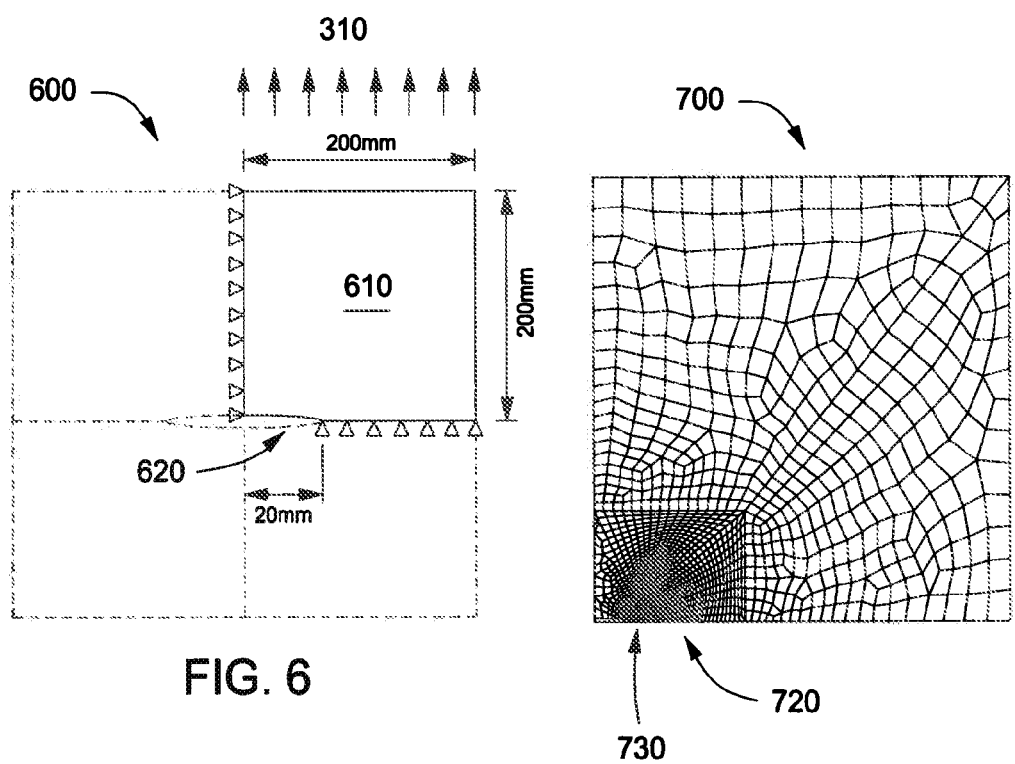
FIG. 6
FIG. 7

SYSTEMS AND METHODS FOR PERFORMING STRESS INTENSITY FACTOR CALCULATIONS USING NON-SINGULAR FINITE ELEMENTS

CROSS-REFERENCE TO RELATED APPLICATIONS

This application claims the benefit of U.S. Provisional Patent Application having Ser. No. 61/301,022, filed on Feb. 3, 2010, which is incorporated by reference herein.

BACKGROUND

1. Field

Embodiments described herein generally relate to fracture mechanics. More particularly, embodiments described herein relate to performing crack analyses using stress intensity factor calculations from non-singular finite elements.

2. Description of the Related Art

Fracture mechanics is an immensely powerful tool that allows rational predictions to be made with regard to the ultimate strength and residual fatigue life of cracked structures. Finite element techniques exist that are appropriate for the analysis of cracks, but they generally rely on the use of specialized crack tip elements. There is a fundamental problem though when it comes to modeling cracks, because the gradient of the stress/stain field is large and approaches infinity at the crack tip. To reproduce this behavior precisely with standard finite elements, an infinitesimally fine mesh would be required. The problem can be overcome with the use of singular, or quarter point, crack tip elements known in the art. These are formulated so that they contain a singularity similar to that found at the crack tip. Many standard finite element programs do not possess these elements, however. Moreover, the parameters needed for fracture mechanics calculations such as the stress intensity factor or the J integral can only be extracted from finite element results with specialized post processing algorithms. Such analyses remain the province of the specialist, therefore, restricting the application of fracture mechanics by the wider engineering community.

There is a need, therefore, for systems and methods that enable the determination of crack tip stress intensity factors for an arbitrarily shaped crack in an arbitrarily shaped solid without requiring the use of an extremely fine crack tip mesh, without the use of specialized crack tip elements, or without complex post processing, and which can be performed using standard finite element software packages known in the art.

BRIEF DESCRIPTION OF THE DRAWINGS

FIG. 5 depicts the representative finite element model having the crack tip zone with global displacement and rotation, according to one or more embodiments.

FIG. 6 depicts a first combination of crack length and plate width that was examined.

FIG. 7 depicts a plot of the initial finite element mesh developed for the first combination of crack length and plate width.

DETAILED DESCRIPTION

Systems and methods are disclosed for determining stress intensity factors. In one or more embodiments, the method can include the steps of defining a crack tip zone about one or more crack tips of one or more arbitrarily shaped cracks in an arbitrarily shaped solid. The one or more crack tip zones can be constrained within a finite element model representation mesh of the arbitrarily shaped solid to provide one or more constrained crack tip zones. The combination of the finite element model representation mesh and the one or more constrained crack tip zones can be processed to determine the stress intensity factor for each of the one or more arbitrarily shaped cracks.

Figure 1:
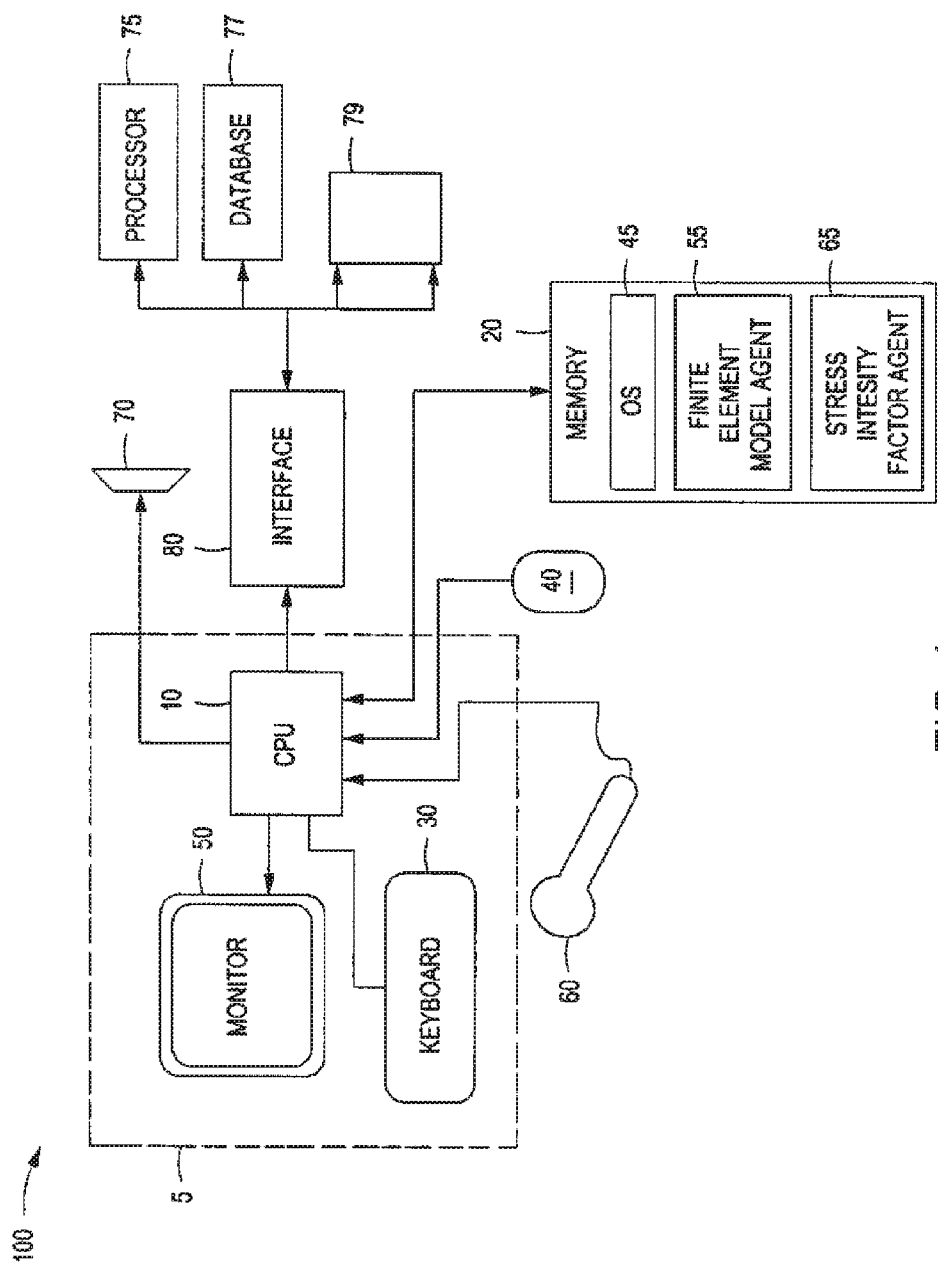
FIG. 1 depicts a representative system for performing crack analyses using stress intensity factor calculations from non-singular finite elements, according to one or more embodiments described.

FIG. 1 depicts a representative system 100 for performing crack analyses using stress intensity factor calculations from non-singular finite elements, according to one or more embodiments described. The system 100 can include a computer 5 can include a central processing unit 10, an input device or keyboard 30, and a monitor 50 on which a software package according to one or more embodiments described herein can be executed. The computer 5 can also include a memory 20 as well as additional input and output devices, for example a mouse 40, a microphone 60, and a speaker 70. The mouse 40, the microphone 60, and the speaker 70 can be used for, among other purposes, universal access and voice recognition or commanding. The monitor 50 can be touch-sensitive to operate as an input device as well as a display device.

The computer 5 can interface with database 77, support computer or processor 75, other databases and/or other processors 79, or the Internet via the interface 80. It should be understood that the term "interface" does not indicate a limitation to interfaces that use only Ethernet connections and refers to all possible external interfaces, wired or wireless. It should also be understood that database 77, processor 75, and/or other databases and/or other processors 79 are not limited to interlacing with computer 5 using network interface 80 and can interface with computer 5 in any means sufficient to create a communications path between the computer 5 and database 77, processor 75, and/or other databases and/or other processors 79. For example, in one or more embodiments, database 77 can interface with computer 5 via a USB interface while processor 75 can interface via some other high-speed data bus without using the network interface 80. In one or more embodiments, the computer 5, processor 75, and other processors 79 can be configured as part of a multiprocessor distributed system.

It should be understood that even though the computer 5 is shown as a platform on which the methods described can be performed, the methods described could be performed on any platform. For example, the many and varied embodiments described herein can be used on any device that has computing capability. For example, the computing capability can include the capability to access any communications bus protocols such that the user can interact with the many and varied computers 5, processors 75, and/or other databases and processors 79 that can be distributed or otherwise assembled. These devices can include, but are not limited to and are presented for illustrative purposes only: supercomputers, arrayed server networks, arrayed memory networks, arrayed computer networks, distributed server networks, distributed memory networks, distributed computer networks, desktop personal computers (PCs), tablet PCs, hand held PCs, laptops, devices sold under the trademark names BLACK-BERRY™ or PALM™, cellular phones, hand held music players, or any other device or system having computing capabilities.

Still referring to FIG. 1, programs can be stored in the memory 20 and the central processing unit 10 can work in concert with at least the memory 20, the input device 30 and the output device 50 to perform tasks for the user. In one or more embodiments, the memory 20 includes any number and combination of memory devices, without limitation, as is currently available or can become available in the art. In one or more embodiments, memory devices can include without limitation, and for illustrative purposes only: database 77, other databases and/or processors 79, hard drives, disk drives, random access memory, read only memory, electronically erasable programmable read only memory, flash memory, thumb drive memory, and any other memory device. Those skilled in the art are familiar with the many variations that can be employed using memory devices and no limitations should be imposed on the embodiments herein due to memory device configurations and/or algorithm prosecution techniques.

The memory 20 can store an operating system (OS) 45, a finite element model agent 55, and a stress intensity factor agent 65. The operating system 45 can facilitate control and execution of software using the CPU 10. Any available operating system can be used in this manner including WINDOWS™, LINUX™, Apple OS™, UNIX™, and the like.

The CPU 10 can execute either from a user request or automatically. In one or more embodiments, the CPU 10 can execute the finite element model agent 55 and/or the stress intensity factor agent 65 when a user requests, among other requests, to determine a stress intensity factor for an arbitrarily shaped crack in an arbitrarily shaped solid. For example, the associated stress intensity factor for the arbitrarily shaped crack in the arbitrarily shaped solid can be determined by defining a crack tip zone about the arbitrarily shaped crack tip and constraining the crack tip zone to behave in a manner consistent with the classical equations of fracture mechanics. The crack tip zone can be constrained using a combination of multi-point constraint equations (MPCs) and a generalized crack tip zone stiffness. The constrained crack tip zone can be combined with a finite element model representation of the remainder of the arbitrarily shaped solid and the combined model can be processed. The stress intensity factor can be determined as part of the processing.

The finite element model agent 55 can be a finite element model software package known in the art. In one or more embodiments, the CPU 10 can execute the finite element model software package when a user requests, among other requests, to determine a stress intensity factor for the arbitrarily shaped crack in the arbitrarily shaped solid. In one or more embodiments, using a finite element model software package known in the art, the stress intensity factor can be determined without the use of the stress intensity factor agent 65. For example, using one or more embodiments of the present invention and a finite element model software package known in the art, a stress intensity factor can be determined for the arbitrarily shaped crack in the arbitrarily shaped solid by defining the crack tip zone about the arbitrarily shaped crack tip. The crack tip zone can be constrained using a combination of multi-point constraint equations (MPCs) and the generalized crack tip zone stiffness. The constrained crack tip zone can be combined with a finite element model representation of the remainder of the arbitrarily shaped solid and the combined model can be processed. The stress intensity factor can be determined during the processing.

It should be noted that the finite element model agent 55 and the stress intensity factor agent 65 can be fully autonomous code sets, partially integrated code sets, or fully integrated code sets and no limitations should be construed from the depiction of the finite element model agent 55 and a stress intensity factor agent 65 as separate agents. It should also be noted that it is not necessary to execute the finite element model agent 55 and the stress intensity factor agent 65 simultaneously nor is it necessary to execute the two agents on the same computer 5.

Figure 2:
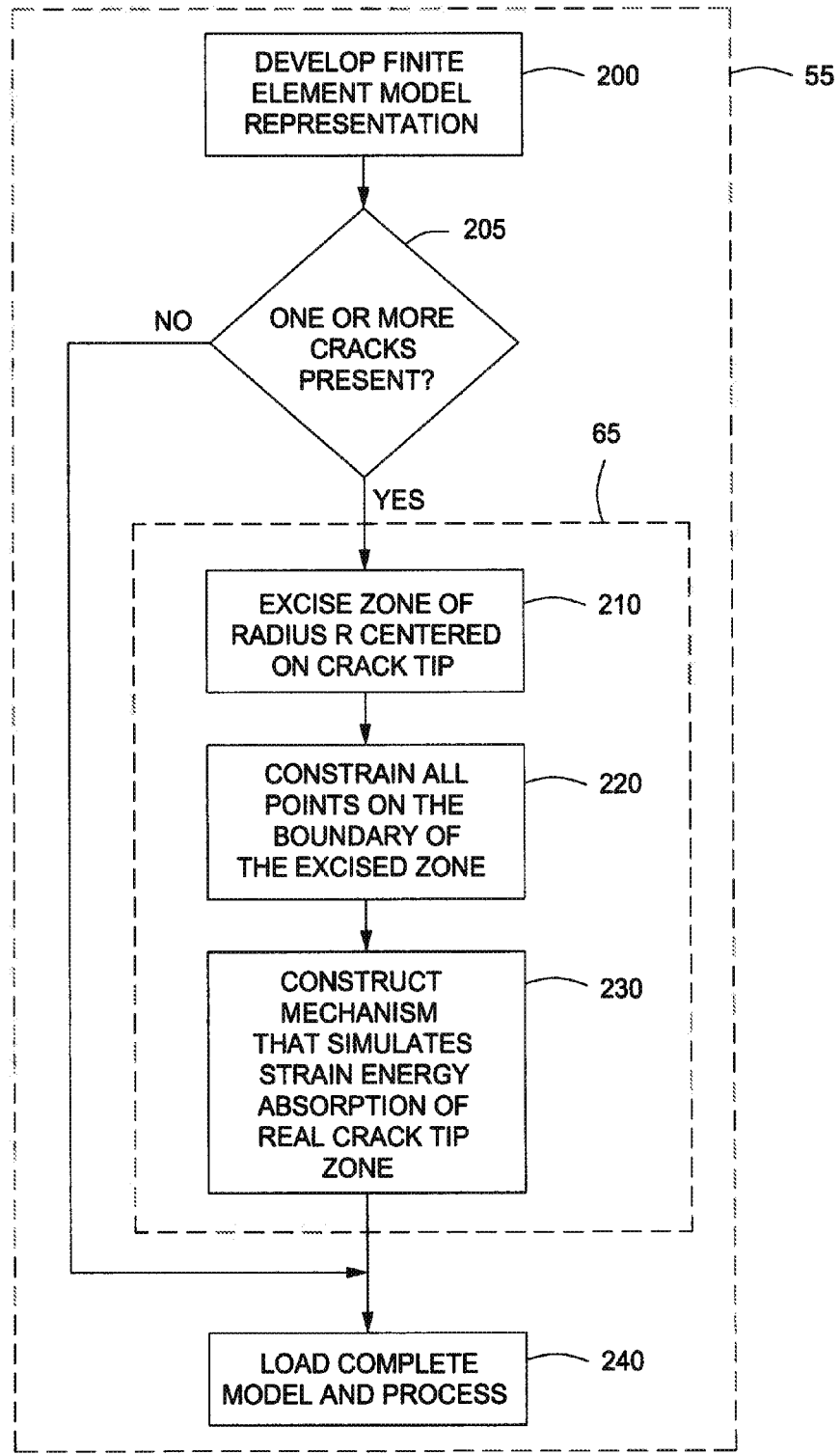
FIG. 2 depicts a representative process flow for determining one or more stress intensity factors for one or more arbitrarily shaped cracks in the arbitrarily shaped solid, according to one or more embodiments.

FIG. 2 depicts a representative process flow for determining one or more stress intensity factors for one or more arbitrarily shaped cracks in the arbitrarily shaped solid, according to one or more embodiments. To perform finite element analysis of the one or more arbitrarily shaped cracks in the arbitrarily shaped solid, not shown, the finite element model agent 55 can be executed and a finite element model representation mesh of at least a portion of the arbitrarily shaped solid can be developed 200. If one or more cracks are present 205 in a given region of the arbitrarily shaped body, the stress intensity agent 65 can be executed 210. The stress intensity agent 65 can excise or remove, from the finite element model representation mesh, the crack tip zone or zone of radius r centered on a crack tip of each of the one or more cracks in the finite element representation mesh. All points on the boundary of the excised zone and/or zones can be constrained 220. A mechanism that simulates the strain energy absorption of the real crack tip zone and/or zones can be constructed 230 for the one or more cracks. The resultant model of each of the one or more crack tip zones can be one or more constrained crack tip zones each corresponding to a given crack in the arbitrarily shaped solid. The constrained crack tip zone and/or zones can be combined with the finite element model representation mesh. In one or more embodiments, the complete model can be loaded in the finite element model agent 55 for processing 240 to determine one or more stress intensity factors associated with the one or more crack tips present within the arbitrarily shaped solid.

For at least one crack within the arbitrarily shaped solid, the crack tip zone can be excluded from the generation of the finite element model representation mesh. In other words, the finite element model representation mesh can be generated without generating the elements within the crack tip zone. Here, the stress intensity agent 65 can be executed 210 to replace the missing crack tip zone with a constrained crack tip zone by constraining all the points on the boundary of the crack tip zone 220 and by constructing a mechanism that simulates the strain energy absorption of the real crack tip zone 230. The constrained crack tip zone can be combined with at least a portion of the finite element model representation mesh. In one or more embodiments, the combined model can be loaded in the finite element model agent 55 for processing 240 to determine the stress intensity factor for the at least one crack present within the arbitrarily shaped solid.

Figure 3:
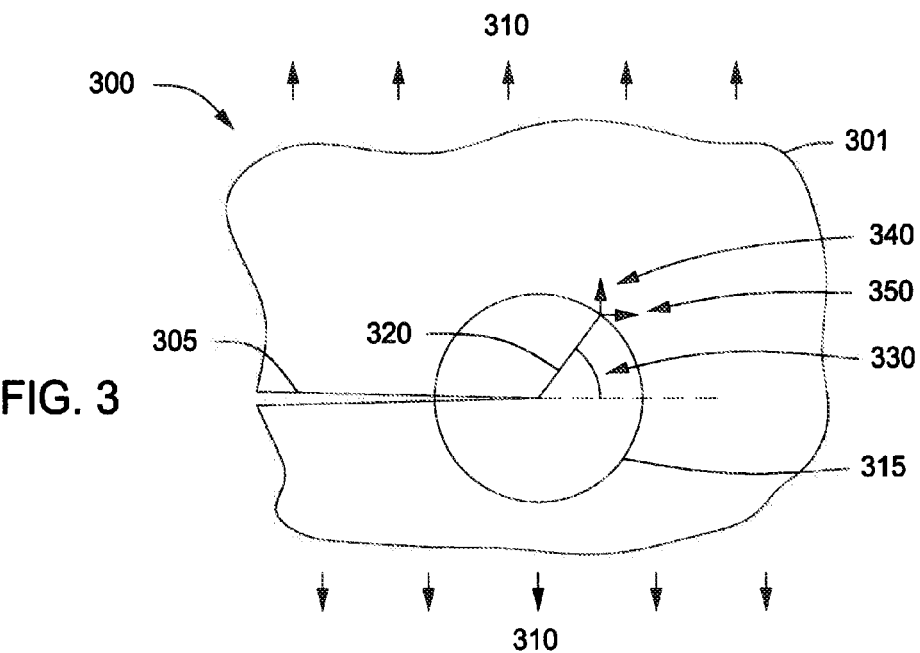
FIG. 3 depicts a representative finite element model of the arbitrarily shaped solid, according to one or more embodiments.

FIG. 3 depicts a representative finite element model 300 of the arbitrarily shaped solid 301, according to one or more embodiments. The representative finite element model 300 can be constructed so as to represent all relevant geometrical features of the arbitrarily shaped solid 301 and a crack 305, except for a relatively small circular region or crack tip zone 315 of radius 320 centered on the crack tip, not shown. It should be noted that in the case of a 3D model, the crack tip zone 315 can be a truncated toroidal shape with cross-sectional radius 320. Under a nominal load 310, the crack tip zone 315 can experience a net deflection (u, v) 340, 350 which can vary with at least radius 320.

Linear elastic fracture mechanics in the analysis of cracks in engineering structures can be based on the assertion that the stresses near the tip of any crack in any linear-elastic body possess a universal distribution, given by a set of approximate equations which become exact at the crack tip. The magnitude of these equations can depend on a term known as the stress intensity factor K. All cracks can be characterized by the value of the stress intensity factor K. Fracture can be said to occur when the stress intensity factor K surpasses a given value, known in the art, dependant upon the material. The crack tip stress field formulations can be described by equations (1) through (3) below for a crack in a body subject to a nominal uniaxial stress σ, 310 normal to the crack plane:

$$\sigma_{xx} = \frac{K}{\sqrt{2\pi r}} \cos\frac{\theta}{2}\left[1 - \sin\left(\frac{\theta}{2}\right)\sin\left(\frac{3\theta}{2}\right)\right] - \{\sigma\} \quad (1)$$

$$\sigma_{yy} = \frac{K}{\sqrt{2\pi r}} \cos\frac{\theta}{2}\left[1 + \sin\left(\frac{\theta}{2}\right)\sin\left(\frac{3\theta}{2}\right)\right] \quad (2)$$

$$\tau_{xy} = \frac{K}{\sqrt{2\pi r}} \sin\frac{\theta}{2}\cos\left(\frac{\theta}{2}\right)\cos\left(\frac{3\theta}{2}\right) \quad (3)$$

where K is the stress intensity factor which is a function of geometry, crack size, and applied loading, with units of stress times the square root of length; r is the radial distance 320 from the crack tip, and θ is the angle 330 measured from the x-axis. For relatively small radii r, the stresses and displacements around the tip of a crack vary approximately only with the value of K. In one or more embodiments, K can be used to characterize any given crack.

The in-plane displacements u' and v' close to the crack tip can be given by the equations (4) and (5) for plane stress conditions:

$$u' = \frac{K}{G}\sqrt{\frac{r}{2\pi}}\cos\frac{\theta}{2}\left[\frac{1-v}{1+v} + \sin^2\frac{\theta}{2}\right] - \left\{r\cos\theta\frac{\sigma}{E}\right\} \quad (4)$$

$$v' = \frac{K}{G}\sqrt{\frac{r}{2\pi}}\sin\frac{\theta}{2}\left[\frac{2}{1+v} - \cos^2\frac{\theta}{2}\right] + \left\{v\,r\sin\theta\frac{\sigma}{E}\right\} \quad (5)$$

and by equations (6) and (7) for plane strain conditions:

$$u' = \frac{K}{G}\sqrt{\frac{r}{2\pi}}\cos\frac{\theta}{2}\left[1 - 2v + \sin^2\frac{\theta}{2}\right] - \left\{r\cos\theta\frac{(1-v^2)}{E}\sigma\right\} \quad (6)$$

$$v' = \frac{K}{G}\sqrt{\frac{r}{2\pi}}\sin\frac{\theta}{2}\left[2 - 2v - \cos^2\frac{\theta}{2}\right] + \left\{v\,r\sin\theta\frac{(1+v)}{E}\sigma\right\} \quad (7)$$

where G is the shear modulus of elasticity, E is Young's modulus, and v is Poisson's ratio (G=E/2(1+v)).

Still referring to FIG. 3, in one or more embodiments, to complete the representative finite element model 300 a mechanism can be placed within the crack tip zone 315 that, within modeling limitations, can mimic the behavior of the material that has been effectively excised from the crack tip zone 315. The mechanism can be nearly indistinguishable from an explicitly modeled crack tip region if the mechanism constrains the displacements on the boundary of the crack tip zone 315 to be at least approximately equal to those of the real crack tip region. Equations (1) through (7) can be used to construct the required mechanism.

Figure 4:
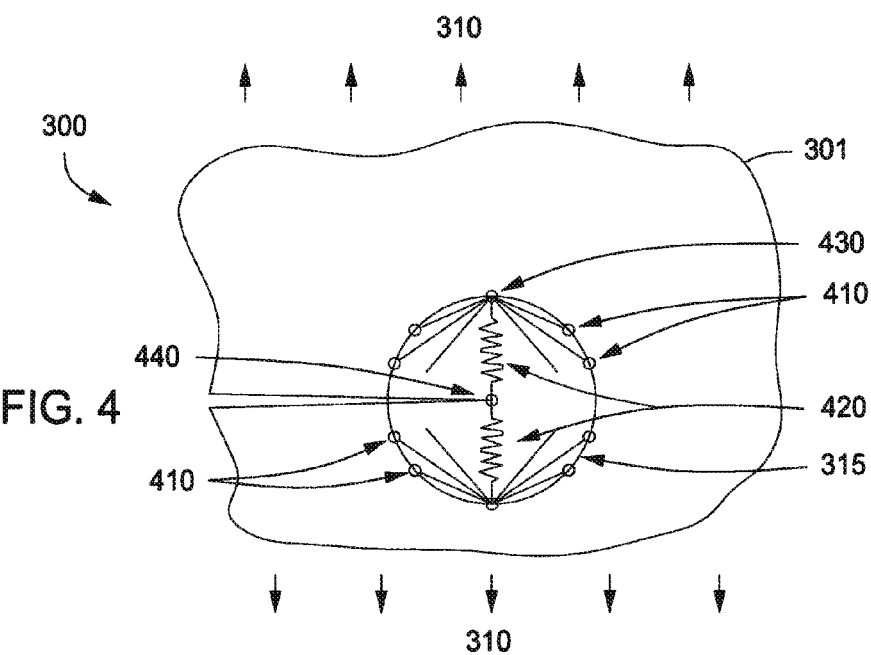
FIG. 4 depicts a representative mechanism that can mimic the reaction of material within the crack tip zone of the arbitrarily shaped solid depicted in FIG. 3, according to one or more embodiments.

FIG. 4 depicts a representative mechanism that can simulate the reaction of material within the crack tip zone 315 of the arbitrarily shaped solid 301 depicted in FIG. 3, according to one or more embodiments. The representative finite element model 300 crack tip zone 315 can be replaced by a system of one or more multi-point constraints (MPCs) 410 about the boundary of the crack tip zone 315 and one or more models of one or more springs 420 (two are shown) or one or more models each including one or more spring functions, each spring or spring function having a spring stiffness k. Each spring stiffness k can be equal to or different from any other spring stiffness k. For example, a first spring stiffness $k_1$ can be equal to a second spring stiffness $k_2$ and different from a third spring stiffness $k_3$, where $k_3$ can be equal to a fourth spring stiffness $k_4$. The one or more springs 420 can be placed between at least a crack tip 440 and a reference point 430. In one or more embodiments, the MPCs can ensure that points on the boundary of the crack tip zone 315 of radius r deform to the deflected shape given by equations (4) through (7) above. The one or more springs 420 can form a mechanism that can represent the strain energy absorbed by an area around the real crack tip corresponding to the crack tip zone 315. In one or more embodiments therefore, under the nominal load 310, the replaced elements can mimic the reaction of the material within the area around the real crack tip corresponding to the crack tip zone 315.

MPCs are known in the art. The MPCs can be used to constrain the deflection at one (dependent) node in the finite element model 300 to be a linear combination of the deflections at an arbitrary number of other (independent) nodes. In one or more embodiments, suitable MPC equations for constraining the boundary of the crack tip zone 315 can be derived using equations (4) through (7).

Each spring 420 can be modeled with a generalized crack tip zone 315 spring stiffness k. The spring stiffness k can be calculated using equations (1) through (7).

FIG. 5 depicts the representative finite element model 300 having the crack tip zone 315 with global displacement and rotation, according to one or more embodiments. In one or more embodiments, a local coordinate system (u, v) 520 can be defined in the finite element model 300 centered on at the crack tip 440. Deflections $(u_r, v_r)$ 530 and $(u_d, v_d)$ 540 can be located at radius 320 and at angle 330 or "θ" along the boundary of the crack tip zone 315. At least one spring 420 can be located between the origin 440 and the reference point 430. Deflection 530 can be located at the reference point 430. The angle 330 can be rotated from the local coordinate system 520 by angle 510 or "ω."

The local coordinate system 520 can be oriented such that the local x-axis can be parallel to the undeformed crack surface and perpendicular to the undeformed crack front, and the local y-axis can be perpendicular to the undeformed crack surface, with reference to FIG. 3 above. Referring to FIG. 3 and FIG. 5, in the undeformed model the finite element model local coordinate system 520 can therefore coincide with the coordinate system implied in equations (4) through (7). However, when the model is loaded, in general, the crack tip zone 315 can be subject to a global deflection $(u_0, v_0)$ and rotation ω which can be reflected in the deflections reported in the post-processed finite element model output, albeit in the local axis system 520. A distinction can be drawn between the deflections (u, v) in the finite element local coordinate system 520, which include the effects of global displacement and rotation, and the deflections (u', v') which can be corrected to remove the global components and can be used in conjunction with equations (4) through (7).

Referring again to FIG. 5, in one or more embodiment, to use equations (4) through (7) to derive at least one set of multi-point constraint equations that constrain the crack tip zone 315, the finite element degree of freedom deflections can be normalized to eliminate the global displacement and rotation of the crack tip zone 315. In one or more embodiments, assuming small displacements and ignoring second order terms, ω can be given by equation (8):

$$\omega = \frac{u_0 - u_r}{r} \qquad (8)$$

Accordingly $u_r'$ and $v_r'$ can be given by equations (9):

$$u_r' = u_r + r\left(\frac{u_0 - u_r}{r}\right) - u_0 = 0 \qquad (9)$$

$$v_r' = v_r - v_0$$

where $u_r'$ and $v_r'$ are the finite element deflections at the reference point 430 (θ=90°) corrected for global displacement and rotation of the crack tip zone. Similarly, at any general angular position θ on the boundary of the crack tip region, $u_r'$ and $v_r'$ can be given by equations (10) and (11) respectively:

$$u_d' = u_d - u_0 + \sin\theta(u_0 - u_r) \qquad (10)$$

$$v_d' = v_d - v_0 - \cos\theta(u_0 - u_r) \qquad (11)$$

Since $u_r'=0$, for plane stress conditions, an equality can be derived as given by equation (12):

$$u_d' - u_r' = u_d - u_0 + \sin\theta(u_0 - u_r) = \frac{K}{G}\sqrt{\frac{r}{2\pi}}\cos\frac{\theta}{2}\left[\frac{1-v}{1+v} + \sin^2\frac{\theta}{2}\right] - \qquad (12)$$

$$\left\{r\cos\theta\frac{\sigma}{E}\right\} - \frac{K}{G\sqrt{2}}\sqrt{\frac{r}{2\pi}}\left[\frac{1-v}{1+v} + \frac{1}{2}\right]$$

Allowing the deflection $v_r$ at point 430 (θ=90°) to be a reference deflection, for plane stress conditions $v_r'$ can be given by equation (13):

$$v_r' = v_r - v_0 = \frac{K}{2G}\sqrt{\frac{r}{\pi}}\left[\frac{2}{1+v} - \frac{1}{2}\right] + \left\{vr\frac{\sigma}{E}\right\} \qquad (13)$$

and for plane strain conditions $v_r'$ can be given by equation (14):

$$v_r' = v_r - v_0 = \frac{K}{2G}\sqrt{\frac{r}{\pi}}\left[2 - 2v - \frac{1}{2}\right] + \left\{vr(1+v)\frac{\sigma}{E}\right\} \qquad (14)$$

In one or more embodiments, the generalized formulation of the multi-point constraint equations can be of the form given by equation (15):

$$u_d = \Sigma a_i u_i \qquad (15)$$

where $u_d$ is the dependent variable (deflection), $u_i$ is an independent variable (deflection) and $a_i$ is a constant. In any given crack problem σ=αK, where α is a constant. Using the results above and putting a=αK, the local x direction multi-point constraint equations can be given by equations (16) through (18) where $u_d$ can be given by equation (16):

$$u_d = \sin\theta u_r + [1-\sin\theta]u_0 + a_u v_r - a_u v_0 \qquad (16)$$

and where, for plane stress conditions $a_u$ can be given by equation (17) and for plain strain conditions $a_u$ can be given by equation (18) respectively:

$$a_u = \frac{2(1+v)\sqrt{\frac{r}{2\pi}}\cos\frac{\theta}{2}\left[\frac{1-v}{1+v} + \sin^2\frac{\theta}{2}\right] - \{r\alpha\cos\theta\} - \sqrt{\frac{r}{\pi}}\left[\frac{3-v}{2}\right]}{\sqrt{\frac{r}{\pi}}\left[\frac{3-v}{2}\right] + vr\alpha} \qquad (17)$$

$$a_u = \frac{2\sqrt{\frac{r}{2\pi}}\cos\frac{\theta}{2}\left[1 - 2v + \sin^2\frac{\theta}{2}\right] - \{r\alpha\cos\theta(1-v)\} - \sqrt{\frac{r}{\pi}}\left[\frac{3-4v}{2}\right]}{\sqrt{\frac{r}{\pi}}\left[\frac{3-4v}{2}\right] + vr\alpha} \qquad (18)$$

The multi-point constraint equations for the local y direction can be given by equations (19) though (21) where $v_d$ can be given by equation (19):

$$v_d = v_0 + (\cos\theta)u_0 - (\cos\theta)u_r + a_v v_r - a_v v_0 \qquad (19)$$

and where, for plane stress conditions $a_v$ can be given by equation (20) and for plane strain conditions $a_v$ can be given by equation (21) respectively:

$$a_v = \frac{2(1+v)\sqrt{\frac{r}{2\pi}}\sin\frac{\theta}{2}\left[\frac{2}{1+v} - \cos^2\frac{\theta}{2}\right] + \{vr\alpha\sin\theta\sigma\}}{\sqrt{\frac{r}{\pi}}\left[\frac{3-v}{2}\right] + \{vr\alpha\}} \qquad (20)$$

$$a_v = \frac{2\sqrt{\frac{r}{2\pi}}\sin\frac{\theta}{2}\left[2 - 2v - \cos^2\frac{\theta}{2}\right] + \{vr\alpha\sin\theta\}}{\sqrt{\frac{r}{\pi}}\left[\frac{3-4v}{2}\right] + \{vr\alpha\}} \qquad (21)$$

In one or more embodiments, $(u_r, v_r)$ and $(u_0, v_0)$ can be the finite element deflections at reference points 430 and 440 respectively. It should be noted that $(u_0, v_0)$ can describe the deflection of the origin 440 connecting springs 420. It should also be noted that deflections $(u_0, v_0)$ can describe the deflections of the origin 440 connecting the spring 420 to the reference point 430 on the boundary of the crack tip tone 315 in the case of a symmetric half crack model.

The precise form of the multi-point constraint equations derived above can be adjusted to suit any finite element software package and/or the finite element model agent 55 and/or the stress intensity agent 65 with reference to FIGS. 1 and 2 above.

Referring again to FIG. 5, in one or more embodiments, to determine the value of the stiffness k of the crack tip zone 315 or the one or more springs 420, the total strain energy contained within the crack tip tone 315 can be determined. As discussed above, the stresses at any point close to the crack tip 440 can be given by equations (1) through (3). The strain energy density ρ, for plane stress conditions, can be given by equation (22) and for plane strain conditions by equation (23) respectively:

$$\rho = \frac{1}{2E}(\sigma_{xx}^2 - 2\nu\sigma_{xx}\sigma_{yy} + \sigma_{yy}^2 + 2(1+\nu)\tau_{xy}^2) \quad (22)$$

$$\rho = \frac{(1+\nu)}{2E}((1-\nu)\sigma_{xx}^2 - 2\nu\sigma_{xx}\sigma_{yy} + (1-\nu)\sigma_{yy}^2 + 2\tau_{xy}^2) \quad (23)$$

The total strain energy per unit thickness contained within the crack tip zone 315 can be given by equation (24):

$$U = \int_0^r \int_{-\pi}^{\pi} \rho \, r \, dr \, d\theta \quad (24)$$

Equations (1) through (3) can each be considered separately with respect to equation (24) to determine the crack tip zone 315 stiffness k. The double integral of $\sigma_{xx}^2$ can be given by equation 25:

$$\iint \sigma_{xx}^2 r \, dr \, d\theta = \quad (25)$$

$$\iint \left\{ \frac{K^2}{2\pi r}\cos^2\frac{\theta}{2}\left[1 - 2\sin\frac{\theta}{2}\sin\frac{3\theta}{2} + \sin^2\frac{\theta}{2}\sin^2\frac{3\theta}{2}\right] - \right. \\ \left. 2\sigma\frac{K}{\sqrt{2\pi r}}\cos\frac{\theta}{2}\left[1 - \sin\frac{\theta}{2}\sin\frac{3\theta}{2}\right] + \sigma^2 \right\} r \, dr \, d\theta$$

Equation (25) can be simplified using the series of mathematical manipulations given by equations (26) through (29), the simplified equation (25) given by equation (30):

$$= \iint \left\{ \frac{K^2}{4\pi r}(1+\cos\theta)\begin{bmatrix} 1-\cos\theta + \cos 2\theta + \\ \frac{1}{4}(1-\cos\theta)(1-\cos 3\theta) \end{bmatrix} - \right. \\ \left. 2\sigma\frac{K}{\sqrt{2\pi r}}\left[\cos\frac{\theta}{2} - \cos\frac{\theta}{2}\left(\frac{\cos\theta}{2} - \frac{\cos 2\theta}{2}\right)\right] + \sigma^2 \right\} r \, dr \, d\theta \quad (26)$$

$$= \iint \left\{ \frac{K^2}{4\pi r}\begin{bmatrix} 1-\cos\theta + \cos 2\theta + \\ \frac{1}{4}(1-\cos\theta)(1-\cos 3\theta) + \\ \cos\theta - \cos^2\theta + \cos\theta\cos 2\theta + \\ \frac{1}{4}\cos\theta(1-\cos 3\theta - \cos\theta + \cos\theta\cos 3\theta) \end{bmatrix} - \right. \\ \left. 2\sigma\frac{K}{\sqrt{2\pi r}}\left[\cos\frac{\theta}{2} - \frac{1}{4}\left(\cos\frac{\theta}{2} - \cos\frac{5\theta}{2}\right)\right] + \sigma^2 \right\} r \, dr \, d\theta \quad (27)$$

$$= \iint \left\{ \frac{K^2}{4\pi r}\begin{bmatrix} 1-\cos\theta + \cos 2\theta + \\ \frac{1}{4}\left(\frac{1-\cos 3\theta - \cos\theta +}{\frac{1}{2}[\cos 2\theta + \cos 4\theta]}\right) + \\ \cos\theta - \frac{1}{2} - \frac{\cos 2\theta}{2} + \frac{\cos 2\theta}{2} + \frac{\cos 3\theta}{2} + \\ \frac{1}{4}\left(\cos\theta - \frac{\cos 2\theta}{2} - \frac{\cos 2\theta}{2}\right) + \\ \frac{1}{4}\left(-\frac{1}{2} - \frac{\cos 2\theta}{2} + \frac{\cos 3\theta}{2} + \frac{\cos\theta}{4} + \frac{\cos 5\theta}{4}\right) \end{bmatrix} - \right. \\ \left. 2\sigma\frac{K}{\sqrt{2\pi r}}\left[\cos\frac{\theta}{2} - \frac{1}{4}\left(\cos\frac{\theta}{2} - \cos\frac{5\theta}{2}\right)\right] + \sigma^2 \right\} r \, dr \, d\theta \quad (28)$$

$$= \int_0^r \int_{-\pi}^{\pi} \left\{ +\frac{K^2}{4\pi r}\begin{bmatrix} \frac{5}{8} + \frac{9\cos\theta}{16} + \frac{3\cos 2\theta}{8} + \\ \frac{3\cos 3\theta}{8} + \frac{\cos 5\theta}{16} \end{bmatrix} - \right. \\ \left. \frac{\sigma}{2}\frac{K}{\sqrt{2\pi r}}\left[3\cos\frac{\theta}{2} + \cos\frac{5\theta}{2}\right] + \sigma^2 \right\} r \, dr \, d\theta \quad (29)$$

$$\iint \sigma_{xx}^2 r \, dr \, d\theta = \frac{5K^2 r}{16} - \frac{65}{15}\sigma\frac{Kr^{3/2}}{\sqrt{2\pi}} + \pi r^2\sigma^2 \quad (30)$$

The double integral for $\sigma_{xx}\sigma_{yy}$ can be given by equation (31) and given as simplified by equation (32):

$$\iint \sigma_{xx}\sigma_{yy} r \, dr \, d\theta = \quad (31)$$

$$\iint \left\{ \frac{K^2}{2\pi r}\cos^2\frac{\theta}{2}\left[1 - \sin^2\frac{\theta}{2}\sin^2\frac{3\theta}{2}\right] - \right. \\ \left. \sigma\frac{K}{\sqrt{2\pi r}}\cos\frac{\theta}{2}\left[1 + \sin\frac{\theta}{2}\sin\frac{3\theta}{2}\right] \right\} r \, dr \, d\theta$$

$$\iint \sigma_{xx}\sigma_{yy} r \, dr \, d\theta = \frac{7K^2 r}{16} - \frac{48}{15}\sigma\frac{Kr^{3/2}}{\sqrt{2\pi}} \quad (32)$$

In one or more embodiments, the double integral for $\sigma_{yy}^2$ can be given by equation (33) and given as simplified by equation (34):

$$\iint \sigma_{yy}^2 r \, dr \, d\theta = \iint \left\{ \frac{K^2}{2\pi r}\cos^2\frac{\theta}{2}\begin{bmatrix} 1+2\sin\frac{\theta}{2}\sin\frac{3\theta}{2} + \\ \sin^2\frac{\theta}{2}\sin^2\frac{3\theta}{2} \end{bmatrix} \right\} r \, dr \, d\theta \quad (33)$$

$$\iint \sigma_{yy}^2 r \, dr \, d\theta = \frac{13K^2 r}{16} \quad (34)$$

In one or more embodiments, the double integral for $\tau_{xy}^2$ can be given by equation (35) and given as simplified by equation (36):

$$\iint \tau_{xy}^2 r \, dr \, d\theta = \iint \left\{ \frac{K^2}{2\pi r}\cos^2\frac{\theta}{2}\sin^2\frac{\theta}{2}\cos^2\frac{3\theta}{2} \right\} r \, dr \, d\theta \quad (35)$$

$$\iint \tau_{xy}^2 r \, dr \, d\theta = \frac{K^2 r}{16} \quad (36)$$

Equations 30, 32, 34, and 36 can be substituted into the expressions for the strain energy per unit thickness equation

(24) to determine the crack tip zone 315 stiffness k. For plane stress conditions, the strain energy per unit thickness can be given by equation (37):

$$U = \frac{1}{2E}\left(\frac{5K^2r}{16} - \frac{64}{15}\sigma\frac{Kr^{3/2}}{\sqrt{2\pi}} + \pi r^2\sigma^2 - 2v\left(\frac{7K^2r}{16} - \frac{48}{15}\sigma\frac{Kr^{3/2}}{\sqrt{2\pi}}\right) + \frac{13K^2r}{16} + 2(1+v)\left(\frac{K^2r}{16}\right)\right) \quad (37)$$

$$= \frac{1}{2E}\left(\frac{K^2r}{4}(5-3v) - \frac{\sigma}{15}\frac{Kr^{3/2}}{\sqrt{2\pi}}(64-96v) + \pi r^2\sigma^2\right)$$

and for plane strain the strain energy per unit thickness can be given by equation (38):

$$U = \frac{1+v}{2E}\left(\begin{array}{l}(1-v)\left(\frac{5K^2r}{16} - \frac{64}{15}\sigma\frac{Kr^{3/2}}{\sqrt{2\pi}} + \pi r^2\sigma^2\right) - \\ 2v\left(\frac{7K^2r}{16} - \frac{48}{15}\sigma\frac{Kr^{3/2}}{\sqrt{2\pi}}\right) + \\ (1-v)\frac{13K^2r}{16} + 2\left(\frac{K^2r}{16}\right)\end{array}\right) \quad (38)$$

$$= \frac{1+v}{2E}\left[K^2r\left(\frac{5}{4} - 2v\right) - \frac{\sigma Kr^{3/2}}{\sqrt{2\pi}}\left(\frac{64}{15} - \frac{32}{3}v\right) + (1-v)\pi r^2\sigma^2\right]$$

The generalized crack tip zone 315 stiffness k can be given by equation (39):

$$k = \frac{2(U/2)}{v_r'^2} \quad (39)$$

For plane stress conditions therefore and noting that $2G=E/(1+v)$ and putting $\sigma=\alpha K$, the crack tip zone 315 stiffness k can be given by equation (40):

$$k = \frac{E\left(\frac{r}{4}(5-3v) - \frac{\alpha}{15}\frac{r^{3/2}}{\sqrt{2\pi}}(64-96v) + \pi r^2\alpha^2\right)}{2\left((1+v)\sqrt{\frac{r}{\pi}}\left[\frac{2}{1+v} - \frac{1}{2}\right] + \{v r\alpha\}\right)^2} \quad (40)$$

and for plane strain conditions, the crack tip zone 315 stiffness k can be given by equation (41):

$$k = \frac{E\left[r\left(\frac{5}{4}-2v\right) - \frac{\alpha r^{3/2}}{\sqrt{2\pi}}\left(\frac{64}{15} - \frac{32}{3}v\right) + (1-v)\pi r^2\alpha^2\right]}{2(1+v)\left(\sqrt{\frac{r}{\pi}}\left[2-2v-\frac{1}{2}\right] + \{v r\alpha\}\right)^2} \quad (41)$$

The strain energy absorbed by the excised material within half of the crack tip zone 315 can be simulated, for example, by one spring 420 disposed between points 430 and 440 when the spring constant k for the spring 420 are given by either equation (40) of (41).

In one or more embodiments, the precise form of the stiffness k equations derived above can be adjusted to suit any finite element software package and/or the finite element model agent 55 and/or the stress intensity agent 65 with reference to FIGS. 1 and 2 above.

It should be noted that all of the derivations of all of the equations of the one or more embodiments described herein are presented for illustrative purposes only. No limitations should be assumed based on these derivations. Any system, method, measurements, or calculations can be used in conjunction with the finite element method to constrain the crack tip zone 315 consistent with one or more embodiments to determine the stress intensity factor K.

Referring again to FIG. 5, in one or more embodiment, an initial estimate of $\alpha=\sigma/K$ can be made. Surprisingly, using one or more embodiments, sample calculations have shown that large errors in initial estimates for $\alpha$ lead to comparatively small errors in the final stress intensity factor K that results from the analysis. One reason for this outcome can be that the crack tip zone 315 mechanism is only part of the complete finite element model; moreover, if radius 320 is relatively small, the effect of $\sigma$ is also relatively small. An initial estimate for a can be used to obtain analysis solutions. In one or more embodiments, a reasonable first estimate for a can be given by equation (42):

$$\alpha = 1/\sqrt{\pi a} \quad (42)$$

where a=the crack depth or half the crack length of the arbitrarily shaped crack. The value for $\sigma$ can be revised from the initial estimate using the results of a preliminary analysis run.

In one or more embodiments, the radius 320 can be selected. The radius 320 can be about 1 mm. The radius 320 can be between about 0.25 mm and 1.5 mm. In one or more embodiments, the radius 320 can also be up to about 10% of the crack depth under study. The radius 320 can be up to about 15% to about 20% of the crack depth under study. The radius 320 can be from a low of about 1%, 2%, 3%, or 4% to a high of about 7%, 8%, 9%, or 10% of the crack depth under study. The radius 320 can be up to about 10% of half the crack length under study. The radius 320 can be up to about 15% or about 20% of half the crack length under study. The radius 320 can be from a low of about 1%, 2%, 3%, or 4% to a high of about 7%, 8%, 9%, or 10% of half the crack length under study.

In one or more embodiments, the number of spring functions can be selected. The number of spring functions can depend on the mesh size in the finite element model. For example, in the case of a semi-elliptical crack, a example of which is described below, the maximum mesh size in the finite element model can be constrained by the desire to maintain reasonable element shapes. In one or more embodiments, one way to maintain reasonable element shapes can be to select a mesh size such that distortions with more than a side length ratio of about 2:1 can be avoided. The mesh size can be selected such that distortions have a side length ratio of less than or equal to about 2 to 1. The mesh size can be selected such that distortions have a side length ratio of from about 1.1 to 1.0 to less than or equal to about 2.0 to 1.0. The mesh size can be selected such that distortions have a side length ratio of from about 0.5 to 1.0 to less than or equal to about 2.0 to 1.0. The mesh size can be selected such that distortions have a side length ratio equal to a low of about 0.5 to 1.0, 0.7 to 1.0, 0.9 to 1.0, 1.0 to 1.0, 1.1 to 1.0, or 1.2 to 1.0 to a high of less than or equal to about 1.5 to 1.0, 1.7 to 1.0, 1.9 to 1.0, 2.1 to 1.0, 2.5 to 1.0, 3.0 to 1.0, 3.5 to 1.0, or higher. Once the mesh size has been selected, the crack length is known, and the value for radius 320 is selected, an initial selection for the number of spring functions can be made. In one or more embodiments, a sensitivity analysis can be performed to reline the mesh size and the number of spring functions selected until there is little or no change between subsequent model analysis results.

The complete model consisting of the finite element model with crack tip zone 315 plus multi-point constraint equations and spring functions can be processed and finite element results can be generated. The reference deflection $v_r'$ can be used to determine the stress intensity factor K. Since $v_r'=v_r-v_0$ and given equations (4) through (7), the stress intensity factor K for plane stress conditions can be determined using equation (43) and for plane strain conditions can be determined using equation (44), respectively:

$$K = \frac{E(v_r - v_0)}{\sqrt{\frac{r}{\pi}}\left[\frac{3-v}{2}\right] + \alpha v r} \quad (43)$$

$$K = \frac{E(v_r - v_0)}{(1+v)\left\{\sqrt{\frac{r}{\pi}}\left[\frac{3-4v}{2}\right] + \alpha v r\right\}} \quad (44)$$

The foregoing discussion can be further described with reference to the following non-limiting examples. For simplicity and ease of description, however, only some of the calculations performed using the methods and systems (described above) are presented here. Two examples are provided that have been trialed on two crack problems for which published results exist: 1) a through crack in a flat finite width plate using plane stress elements, and 2) a semi-elliptical surface crack in a finite thickness and finite width plate using solid elements.

In the first example, the through crack in a flat finite width plate using plane stress elements was analyzed. The Super Element Structural Analysis Modules (SESAM) finite element program was used with SESAM Type 28 elements. The SESAM Type 28 elements are 8 noded Subparametric Curved Quadrilateral elements with 6 degrees of freedom at each node. The elements have a plane stress formulation and so one or more of the plane stress versions of the equations described above were used.

Figure 8:
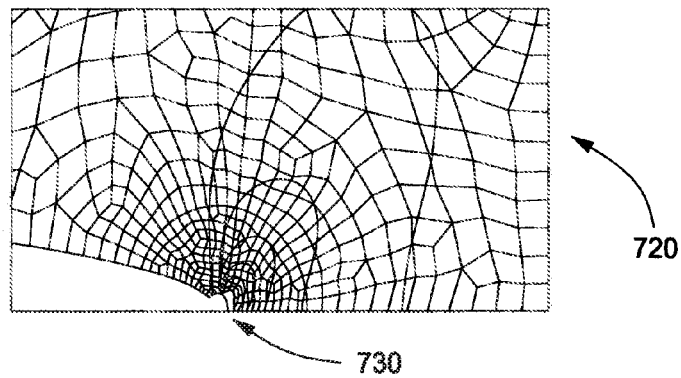
FIG. 8 depicts a close up of the initial finite element mesh for a crack tip region.

FIG. 6 depicts a first combination of crack length and plate width that was examined. The plate 600 has full dimensions of 400 mm by 400 mm and includes a through crack 620 with a nominal length of 40 mm. As the crack/plate geometry possesses two planes of symmetry, only one quarter of the plate 600 was modeled with finite elements. The modeled portion 610 was placed under a simulated nominal stress 310. Boundary conditions were imposed on the cut lines to suppress in-plane rotations and displacements normal to the plane of symmetry. FIG. 7 depicts a plot of the initial finite element mesh developed for the first combination of crack length and plate width. FIG. 8 depicts a close up of the initial finite element mesh for a crack tip region.

Referring to FIG. 7 and FIG. 8, the initial finite element mesh 710 includes the crack tip region 720 and the crack tip zone 730. No elements were modeled within the crack tip zone 730. The crack tip zone 730 had a radius of r=1 mm from the position of the crack tip. Eight evenly spaced elements were placed around the perimeter of the upper half of the modeled crack tip zone 730 and 16 MPC equations were used. A spring with spring constant k=15.5 GN/m was placed between the node at θ=90° and the plane of symmetry of the crack. The applied nominal stress was 1 MPa. The element thickness was input as 100 mm, although this had no effect on the plane stress formulation of the elements. A nm of the finite element model plus MPC and spring constraints was performed.

A second run was performed using a plate of the same size as plate 600 with a 160 mm long crack, with reference to FIG. 6. A third run was performed with an extended crack plate, not shown, with full dimensions 800 mm by 400 mm with a through crack of nominal length 320 mm. For similar reason discussed above, only one quarter of the extended crack plate was modeled with finite elements. The results from all three runs were compared with those given in BS 7910: 2005 (BS 7910. "Guide to methods for assessing the acceptability of flaws in metallic structures," British Standards Institution. Jul. 27, 2005).

The results for the 20 mm long crack in the 400 mm long plate and the 160 mm long crack in the 800 mm long plate were within 1% of the BS 7910 values. The result for the 160 mm long crack in the 400 mm long plate were about 10% higher than the BS 7910 value.

In the second example, an analysis was performed on the semi-elliptical surface crack in a finite thickness and finite width plate using SESAM Type 20 elements. The SESAM Type 20 elements are 20 node Isoparametric Hexahedron elements with 20×3 degrees of freedom.

Figure 9:
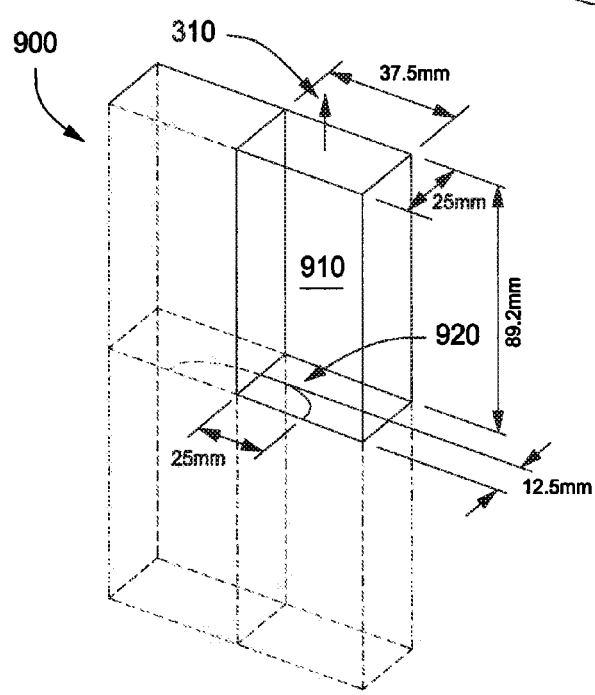
FIG. 9 depicts the semi-elliptical surface crack in the finite thickness and finite width plate.

FIG. 9 depicts the semi-elliptical surface crack in the finite thickness and finite width plate. The finite plate 900 has full dimensions of 75 mm wide by 178.4 mm high by 25 mm thick. The plate 900 includes the semi-elliptical surface crack 920. As the crack/plate geometry possesses two planes of symmetry, only one quarter of the plate 910 was modeled with finite elements. The modeled portion 910 was placed under a simulated nominal stress 310.

Figure 10:
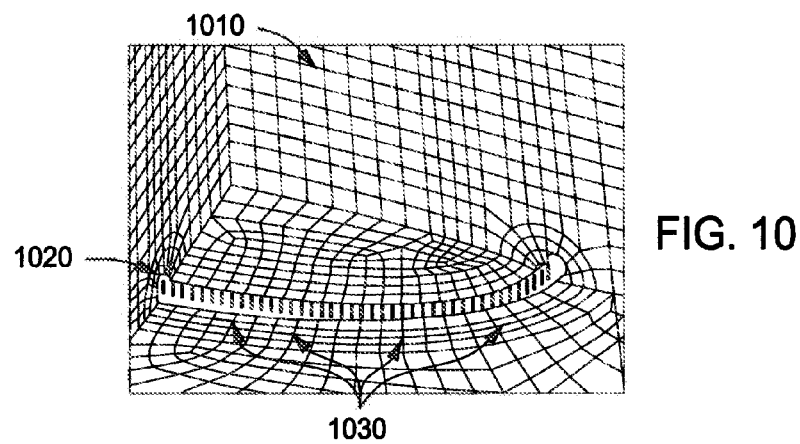
FIG. 10 depicts a close up of the finite element mesh of the crack tip region for the semi-elliptical surface crack.

FIG. 10 depicts a close up of the finite element mesh of the crack tip region for the semi-elliptical surface crack. The crack tip region 1010 includes a crack tip zone 1020, 1030. For the crack tip region 1010, plane strain versions of the equations described above were used at all points along the crack tip zone 1030 except where the crack intersects the front surface 1020 of the plate. At the front surface 1020 the plane stress formulations were used.

As with the through crack models, the crack tip zone 1020, 1030 was modeled with a radius of r=1 mm and 8 elements were arranged around the periphery of the region representing the upper half of the crack tip zone 1020, 1030. Twenty half rings of approximately evenly spaced elements were arranged along the modeled crack front 1030. To calculate the spring stiffness constants the effective crack tip zone 1020, 1030 thickness was taken to be two-thirds of the element spacing for element mid-side nodes, one-third of the element spacing for corner nodes in the interior of the model, and, one-sixth of the element spacing for corner nodes at the front 1020 and cut surfaces. This uneven distribution of spring constants results from the particular shape functions used in the formulation of the isoparametric elements. The MPC equations and spring constants for the model were generated using a standard computer spreadsheet known in the art. The combined model was processed. The results were compared to those given in BS 7910: 2005.

The semi-elliptical crack results quoted in BS 7910 are stated to be valid for both clamped and pinned plate end support conditions. The second example analysis shows a slight difference in the results between the clamped and pinned conditions—the pinned end conditions giving slightly higher stress intensity factors at both the deepest point of the crack front and at the point where it intersects the surface. The clamped plate results give the best agreement with the BS 7910 values at the deepest point, although the result at the surface point is lower than the code values. It should be noted that if the stress intensity factor is evaluated one element inboard of the surface point, where the plane strain formulations are used, a higher stress intensity factor is obtained in closer agreement with the BS 7910 result. It should also be noted that the BS 7910 results in part rely on a semi-empirical correction factor to account for the large crack size in relation to the plate cross-sectional area.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A computer implemented method for determining one or more stress intensity factors, the method comprising:
    defining one or more crack tip zones about one or more crack tips of one or more arbitrarily shaped cracks in a finite element model representation mesh of an arbitrarily shaped solid;
    constraining, by a computer, the one or more crack tip zones within a finite element model representation mesh of the arbitrarily shaped solid to provide one or more constrained crack tip zones, wherein constraining the one or more crack tip zones comprises generating one or more multi-point constraint equations and one or more crack tip zone stiffness values to define the one or more constrained crack tip zones;
    wherein the one or more multi-point constraint equations are a function of a square root of a ratio of a radial distance from the crack tip over two times pi;
    processing, by the computer, a combination of the finite element model representation mesh and the one or more constrained crack tip zones; and
    determining, by the computer, a stress intensity factor for each of the one or more arbitrarily shaped cracks, wherein an initial estimate of a ratio of a uniaxial stress for a first arbitrarily shaped crack over the stress intensity factor for the first arbitrarily shaped crack is equal to the reciprocal of the square root of the product of pi times a crack depth of the first arbitrarily shaped crack, the initial estimate being employed in the one or more multi-point constraint equations during a preliminary analysis run and, based on a result of the preliminary analysis run, a value for the uniaxial stress of the first arbitrarily shaped crack is updated.

2. The method of claim 1, wherein the one or more crack tip zones is within a three dimensional model and the crack tip zone is in the shape of a truncated toroid.

3. The method of claim 1, wherein at least one multi-point constraint equation is utilized to generate one or more multi-point constraints to constrain at least two points about a boundary of each of the corresponding one or more crack tip zones;
    wherein at least one crack tip zone stiffness value is utilized to generate one or more models representing the strain energy absorbed by each of the corresponding one or more crack tips; and
    combining each of the one or more multi-point constraints with each of the corresponding models representing the strain energy absorbed by the one or more crack tips.

4. The method of claim 3, wherein at least one of the models representing the strain energy absorbed by the one or more crack tips comprises a model of one or more springs having a spring stiffness that represents the strain energy absorbed by at least one of the one or more crack tips.

5. The method of claim 1, wherein a mesh size of the initial finite element model representation mesh is selected such that distortions have a side length ratio of less than or equal to 2 to 1.

6. The method of claim 1, wherein a radius of each of the one or more crack tip zones is 1% to 10% of a crack depth of each of the corresponding one or more arbitrarily shaped cracks.

7. The method of claim 1, wherein a radius of each of the one or more crack tip zones is 1% to 10% of half a crack length of each of the corresponding one or more arbitrarily shaped cracks.

8. The method of claim 1, further comprising generating the finite element model representation mesh of the arbitrarily shaped solid without generating finite elements within the one or more crack tip zones.

9. The method of claim 1, further comprising generating the finite element model representation mesh of the arbitrarily shaped solid; and
    deleting from the finite element model representation mesh the generated finite elements corresponding to the one or more crack tip zones.

10. A computer-implemented method for determining one or more stress intensity factors, the method comprising:
    defining one or more crack tip zones about one or more crack tips of one or more arbitrarily shaped cracks in an arbitrarily shaped solid;
    generating, by the computer, one or more multi-point constraints, each to constrain at least two points about a boundary of each of the corresponding one or more crack tip zones within a finite element model representation mesh of the arbitrarily shaped solid;
    generating, by the computer, one or more models, each that represents a strain energy absorbed by each of the corresponding one or more crack tips;
    wherein at least one of the models representing the strain energy absorbed by at least one of the one or more crack tips comprises a model of one or more springs having a spring stiffness that represents the strain energy absorbed by at least one of the one or more crack tips;
    combining, by the computer, each of the one or more multi-point constraints with each of the corresponding models for each of the one or more crack tips to provide one or more constrained crack tip zones;
    processing, by the computer, the combination of the finite element model representation mesh and the one or more constrained crack tip zone; and
    determining, by the computer, a stress intensity factor for each of the one or more arbitrarily shaped cracks, wherein an initial estimate of a ratio of a uniaxial stress for a first arbitrarily shaped crack over the stress intensity factor for the first arbitrarily shaped crack is equal to the reciprocal of the square root of the product of pi times a crack depth of the first arbitrarily shaped crack, the initial estimate being employed in the one or more multi-point constraint equations during a preliminary analysis run and, based on a result of the preliminary analysis run, a value for the uniaxial stress of the first arbitrarily shaped crack is updated.

11. The method of claim 10, further comprising generating, by the computer, the finite element model representation mesh of the arbitrarily shaped solid without generating finite elements within the one or more crack tip zones.

12. The method of claim 11, wherein a mesh size of the initial finite element model representation mesh is selected such that distortions have a side length ratio of less than or equal to 2 to 1.

13. The method of claim 10, further comprising:
generating, by the computer, the finite element model representation mesh of the arbitrarily shaped solid; and
deleting, by the computer, from the finite element model representation mesh finite elements corresponding to the one or more crack tip zones.

14. The method of claim 13, wherein The mesh size of the initial finite element model representation mesh is selected such that distortions have a side length ratio of less than or equal to 2 to 1.

15. A system for determining stress intensity factors, the system comprising:
a processor;
a non-transitory memory in electronic communication with the processor; and
one or more code sets stored in the non-transitory memory, the code sets being executable by the processor to:
define one or more crack tip zones about one or more crack tips of one or more arbitrarily shaped cracks in an arbitrarily shaped solid; and
constrain the one or more crack tip zones within a finite element model representation mesh of the arbitrarily shaped solid to provide one or more constrained crack tip zones;
wherein to constrain the one or more crack tip zones comprises the processor generating one or more multi-point constraint equations and one or more crack tip zone stiffness values to define the one or more constrained crack tip zones;
wherein the one or more multi-point constraint equations are a function of a square root of a ratio of a radial distance from the crack tip over two times pi;
process the combination of the finite element model representation mesh and the one or more constrained crack tip zones; and
determine a stress intensity factor for each of the one or more arbitrarily shaped cracks, wherein an initial estimate of a ratio of a uniaxial stress for a first arbitrarily shaped crack over the stress intensity factor for the first arbitrarily shaped crack is equal to the reciprocal of the square root of the product of pi times a crack depth of the first arbitrarily shaped crack, the initial estimate being employed in the one or more multi-point constraint equations during a preliminary analysis run and, based on a result of the preliminary analysis run, a value for the uniaxial stress of the first arbitrarily shaped crack is updated.

16. The system of claim 15, wherein constraining the one or more crack tip zones comprises generating one or more multi-point constraints, each to constrain at least two points about a boundary of each of the corresponding one or more crack tip zones;
generating one or more models, each model representing the strain energy absorbed by each of the corresponding one or more crack tips; and
combining each of the one or more multi-point constraints with each of the corresponding models representing the strain energy absorbed by each of the one or more crack tips.

17. The system of claim 15, further comprising the code sets being executable by the processor to generate the finite element model representation mesh of the arbitrarily shaped solid.

* * * * *